US012806343B2

(12) United States Patent
Jaber

(10) Patent No.: US 12,806,343 B2
(45) Date of Patent: Nov. 24, 2026

(54) SYSTEMS AND METHODS FOR NEEDLELESS INJECTION

(71) Applicant: JABER MEDICAL, PLLC, West University Place, TX (US)

(72) Inventor: Noor Mahmoud Jaber, West University Place, TX (US)

(73) Assignee: JABER MEDICAL, PLLC, West University Place, TX (US)

( * ) Notice: Subject to any disclaimer, the term of this patent is extended or adjusted under 35 U.S.C. 154(b) by 698 days.

(21) Appl. No.: 18/044,620

(22) PCT Filed: Sep. 9, 2021

(86) PCT No.: PCT/US2021/071402
§ 371 (c)(1),
(2) Date: Mar. 9, 2023

(87) PCT Pub. No.: WO2022/056533
PCT Pub. Date: Mar. 17, 2022

(65) Prior Publication Data

US 2023/0372626 A1 Nov. 23, 2023

Related U.S. Application Data

(60) Provisional application No. 62/706,777, filed on Sep. 9, 2020.

(51) Int. Cl.
*A61M 5/30* (2006.01)
*A61M 5/315* (2006.01)

(52) U.S. Cl.
CPC ...... *A61M 5/3007* (2013.01); *A61M 5/31511* (2013.01); *A61M 2205/332* (2013.01)

(58) Field of Classification Search
CPC .................. A61M 5/30; A61M 5/3007; A61M 2205/3331; A61M 2205/50; A61M 5/48; A61M 5/482
See application file for complete search history.

(56) References Cited

U.S. PATENT DOCUMENTS 6,056,716 A 5/2000 D'Antonio et al.
6,102,896 A * 8/2000 Roser ...................... A61M 5/30 604/218

(Continued)

OTHER PUBLICATIONS

International Search Report and Written Opinion for International Application No. PCT/US2021/071402, mailed Dec. 22, 2021.

(Continued)

*Primary Examiner* — Bradley J Osinski
(74) *Attorney, Agent, or Firm* — Womble Bond Dickinson (US) LLP

(57) ABSTRACT

Systems and methods to allow for a needleless nozzle to attach to a standard syringe. The standard or typical syringe insertable into a housing. The housing including an actuator to transfer generated mechanical energy to a plunger of a standard syringe to deliver a specified injectable via needleless injection. In embodiments, a needleless injection system includes a syringe having a barrel and a needleless nozzle. The barrel is designed or reinforced to withstand pressure necessary for needleless injection without deformation of the barrel. The needleless nozzle is configured to removeably attach to a proximal end of the barrel and to facilitate needleless injection of an injectable.

20 Claims, 12 Drawing Sheets

(56) References Cited

U.S. PATENT DOCUMENTS

| | | | | |
|---|---|---|---|---|
| 2002/0055712 | A1* | 5/2002 | Neracher .......... | A61M 5/31525 604/153 |
| 2004/0186432 | A1 | 9/2004 | Barry et al. | |
| 2009/0157039 | A1 | 6/2009 | Lenzner et al. | |
| 2012/0253272 | A1 | 10/2012 | Menassa | |
| 2017/0065769 | A1 | 3/2017 | Hemond et al. | |
| 2017/0281875 | A1* | 10/2017 | Piehl .................. | A61M 5/1782 |
| 2019/0143047 | A1* | 5/2019 | Jazayeri ............ | A61M 5/31513 604/222 |
| 2021/0338402 | A1* | 11/2021 | Magyar .................. | G16H 20/17 |

OTHER PUBLICATIONS

INJEX30 needle free injection system Aug. 29, 2019 (INJEX Pharma GmbH) Aug. 29, 2019 (Aug. 29, 2019) [online] retrieved from <URL: https://www.youtube.com/watch?v=Q8FJEtKCELc>.

* cited by examiner

SYSTEMS AND METHODS FOR NEEDLELESS INJECTION

CROSS-REFERENCE TO RELATED APPLICATION

This application is a U.S. National Phase Under 35 U.S.C. § 371 of International Application No. PCT/US2021/071402, titled "SYSTEMS AND METHODS FOR NEEDLELESS INJECTION," filed Sep. 9, 2021, which claims the benefit of, and priority to, U.S. Provisional Patent Application Ser. No. 62/706,777, filed Sep. 9, 2020. The entire contents of these applications are incorporated herein by reference.

FIELD OF DISCLOSURE

Embodiments of this disclosure relate to needleless injection, and more particularly, to systems and methods for needleless injection systems that utilize a standard syringe for delivery.

BACKGROUND

Standard syringes are generally single use and meant to be discarded after use on a subject. Further, standard syringes are usually comprised of a polymer or plastic. Such a syringe may deform or burst if a high enough pressure is created during an injection, particularly a needleless injection. Further still, standard syringes are low cost and readily available in a multitude of sizes.

Needleless injections typically require a high force and/or velocity for an injectable to penetrate a subject's skin. The further or deeper an injectable is required to be injected (e.g., to subcutaneous tissue or muscular tissue), the more force and/or velocity may be required. Such a force and/or velocity may create a pressure too great for a standard syringe. As such, needleless injection systems typically use proprietary syringes or ampules. Such proprietary syringes or ampules are only usable in a corresponding needleless injection system and are usually high cost as compared to a standard syringe.

SUMMARY

Accordingly, Applicant has recognized a need for systems and methods to provide needleless injections using standard syringes and to provide a needleless injection system to deliver an injectable with greater ease and at lower than typical cost. The present disclosure is directed to embodiments of such systems and methods.

Embodiments disclosed herein are designed to decrease needle stick injuries, through the use of needleless injections, while further decreasing the cost and increasing accessibility, well as ease of use, of needleless injections. Embodiments of a needleless injection system described herein may be used with any size and type of standard syringe, thus enabling increased access to needleless injections. Embodiments of the needleless injection systems may offer ease and automation of a needleless injection, thus offering less opportunities for human error in all parts of the injection process (e.g., such as during dosing, injecting, or any other part of the process).

Accordingly, an embodiment of the disclosure is directed to a needleless injection system. The needleless injection system includes a housing. The housing can include an opening, access door, or aperture to allow for insertion of a standard syringe. The housing can further include an adjustable retention portion to accept varying sizes of a standard syringe. The housing can include an actuator. The actuator can include a piston. The actuator can retract the piston to fill an inserted syringe and advance the piston to eject the injectable in a syringe (e.g., inject the injectable into a subject). The housing can further include a power supply, fuel supply, and/or energy supply for the piston and actuator.

In another embodiment, the housing includes a needleless nozzle. The needleless nozzle can be attached to the housing and may be removable. As the standard syringe is inserted into the needleless injection system, an aperture at a proximal end of a barrel of the standard syringe may align with the needleless nozzle. In another example, the needleless nozzle attaches, prior to insertion into the housing, to the syringe via a fitting located at the aperture at the proximal end of the barrel. In another example, the needleless nozzle attaches to the syringe via a friction force fitting, a custom fitting, or other type of fitting. In another embodiment, the piston includes a connector to attach to the end of a plunger included in the standard syringe (e.g., the standard syringe including a plunger). The plunger enters the standard syringe at an aperture at the distal end of the barrel of a standard syringe. Upon insertion of the standard syringe into the needleless injection system, the actuator can position the piston adjacent to the plunger. In an example, the piston's connector attaches to the end of the plunger, thus allowing the piston to move the plunger into and out of the barrel of the standard syringe.

In another embodiment, the housing includes a controller to determine the velocity and/or force to allow for the ejection of the injectable, based on type of injectable, amount of injectable, a level of injection, and/or a location of where the injection will occur on the subject. In an example, the type of injectable and location of where the injection will occur on the subject is obtained by sensors located throughout the needleless injection system. In another example, the controller connects to an input/output of the needleless injection system. The controller may gather data through the input/output regarding a subject and medication. In another example, based on the gathered data, the controller may set the velocity for delivery of the injectable (e.g., injection). In another example, the data may be provided or received from a database (e.g., the database including electronic medical records (EMR), as well as velocity and/or force profiles). In another example, the controller may send data, the data based on the actual delivery of the injectable to the subject, to the database. In another example, the controller connects, via a second input/output, to a user interface. The user interface may allow for data relevant to delivery of injectable to be entered into the controller.

In another embodiment of the present disclosure, a needleless injection system includes a syringe having a barrel and a needleless nozzle. The barrel of the syringe designed or reinforced to withstand pressures necessary for needleless injection without deformation of the barrel. The needleless nozzle is configured to removeably attach to a proximal end of the barrel. The needleless nozzle is for facilitating needleless injection of an injectable.

In embodiments, the needleless injection system includes a reinforced plunger that is capable of producing linear forces within the barrel that is suitable for intradermal, subcutaneous, or intramuscular needleless injection. The reinforced plunger may include a piston and a base. The piston may be configured to linearly translate through a circumferential spacer chamber defined by the barrel. The reinforced plunger may be capable of withstanding at least 50 newtons of linear force.

In certain embodiments, the needleless injection system includes a sleeve configured to receive the barrel of the syringe. The sleeve reinforcing the barrel to prevent deformation of the barrel during needleless injection. The barrel of the syringe is designed to withstand pressures necessary for needleless injection without deformation of the barrel. The barrel may be designed or reinforced to withstand at least 1 mega Pascal of pressure.

In some embodiments, the needleless nozzle is configured to frictionally attached to the proximal end of the barrel. The needleless nozzle may include a fitting that is configured to interface with a complementary fitting of the proximal end of the barrel. The needleless nozzle may define an outlet in a range of 50 microns to 500 microns.

In certain embodiments, the needleless injection system includes a standard syringe. The standard syringe includes a barrel and a plunger. The barrel of the standard syringe is received within the sleeve. The barrel may have a proximal end and the needles nozzle may be attached to the proximal end of the barrel. The barrel may be formed having insufficient tensile strength to provide injection forces suitable for intradermal, subcutaneous, or intramuscular needleless injection without deformation.

In particular embodiments, the needleless nozzle includes a tip and an outer circumference. The tip may include an outlet for delivering an injectable. The tip and the outer circumference may define a circumferential spacer therebetween. The circumferential spacer is configured to create space between a subject receiving the injectable and the tip.

In embodiments, the needleless injection system includes an actuator that is configured to connect to a plunger of the syringe to translate the plunger within the barrel of the syringe. The needleless injection system may include a controller that is in signal communication with the actuator. The controller may determine a velocity and a force for an injection based on an amount of an injectable and a level for injection. The controller may transmit the determined velocity and force to the actuator to initiate injection.

In another embodiment of the present disclosure, a needleless injection system includes a housing, a needleless nozzle, an actuator, and a controller. The housing includes an opening to allow for removal and insertion of a syringe. The syringe may include a barrel and a plunger. The barrel has a proximal end and an open distal end. The plunger inserted through the open distal end. The needleless nozzle is configured to removeably attach to the proximal end of the barrel. The actuator is connected to the plunger to transfer mechanical energy to the plunger to discharge the injectable from the chamber. The controller is in signal communication with the actuator. The control is configured to determine a velocity and force for the injection based on an amount of a specified injectable for the injection and a level or distance for the injection. The controller is configured to transmit the velocity and force to the actuator in response to an initiation of the injection.

In embodiments, the needleless injection system includes a supply to provide the injectable to the actuator to generate mechanical energy based on a control signal from the controller. The actuator may be capable of transferring mechanical energy to the plunger to draw the injectable into the chamber. The housing may include a retention system for securing the syringe within the housing. The actuator may be an electro-pneumatic motor. The actuator may include an electric motor.

In certain embodiments, the needleless injection system includes a sleeve for enclosing the barrel to prevent the barrel from deforming.

In some embodiments, the needleless injection system includes an electrohydraulic motor includes the actuator and a piston. The controller may be in signal communication with a database that includes a velocity profile for an injection. The controller may determine the velocity based on the velocity profile.

In another embodiment of the present disclosure, a needleless injection system includes a housing, a needleless nozzle, an actuator, and a controller. The housing includes an opening to allow for removal of and insertion of a standard syringe. The standard syringe includes a barrel and a plunger. The barrel has a proximal end and an open distal end. The plunger is insertable through the open distal end. The needleless nozzle is configured to removeably attached to the proximal end of the barrel. The actuator includes a piston that is disposed within the housing. The piston is configured to physically interact with the plunger to translate the plunger relative to the barrel. The controller is in signal communication with the actuator. The controller is configured to determine a velocity and force for an injection based on an amount of an injectable for the injection and a level for the injection. The controller is configured to transmit the velocity and force to the actuator in response to an initiation of the injection.

In embodiments, the needleless injection system includes a supply to provide the injectable to the actuator to generate mechanical energy based on the control signal. The housing includes a retention mechanism to secure the standard syringe within the housing.

In certain embodiments, the needleless injection system includes an integrated sleeve for enclosing the barrel to prevent the barrel from deforming.

In another embodiment of the present disclosure, a needleless injection system for a standard syringe including a barrel having a proximal end including a needleless nozzle that is configured to removeably attach to the proximal end of the barrel. The needleless nozzle is configured to generate force necessary to enable needleless injection from a standard syringe.

In embodiments, the needleless nozzle is configured to frictionally attached to the proximal end of the barrel. The needleless nozzle may include a fitting that is configured to interface with a complementary fitting of the proximal end of the barrel. The needleless nozzle may define an outlet in a range of 50 microns to 500 microns.

In some embodiments, the needleless injection system includes a sleeve that is configured to receive the barrel therein. The sleeve is for preventing deformation of the barrel.

In certain embodiments, the needleless injection system includes a reinforced plunger that is capable of producing linear forces within the barrel suitable for intradermal, subcutaneous, or intramuscular needleless injection. The reinforced plunger may include a piston and a base. The piston may be configured to linearly translate through a chamber defined by the barrel.

Still other aspects and advantages of these embodiments and other embodiments, are discussed in detail herein. Moreover, it is to be understood that both the foregoing information and the following detailed description provide merely illustrative examples of various aspects and embodiments, and are intended to provide an overview or framework for understanding the nature and character of the claimed aspects and embodiments. Accordingly, these and other objects, along with advantages and features of the present disclosure herein disclosed, will become apparent through reference to the following description and the accompanying drawings. Furthermore, it is to be understood that the features of the various embodiments described herein are not mutually exclusive and may exist in various combinations and permutations.

BRIEF DESCRIPTION OF DRAWINGS

These and other features, aspects, and advantages of the disclosure will become better understood with regard to the following descriptions, claims, and accompanying drawings. It is to be noted, however, that the drawings illustrate only several embodiments of the disclosure and, therefore, are not to be considered limiting of the scope of the disclosure.

DETAILED DESCRIPTION

Figure 1:
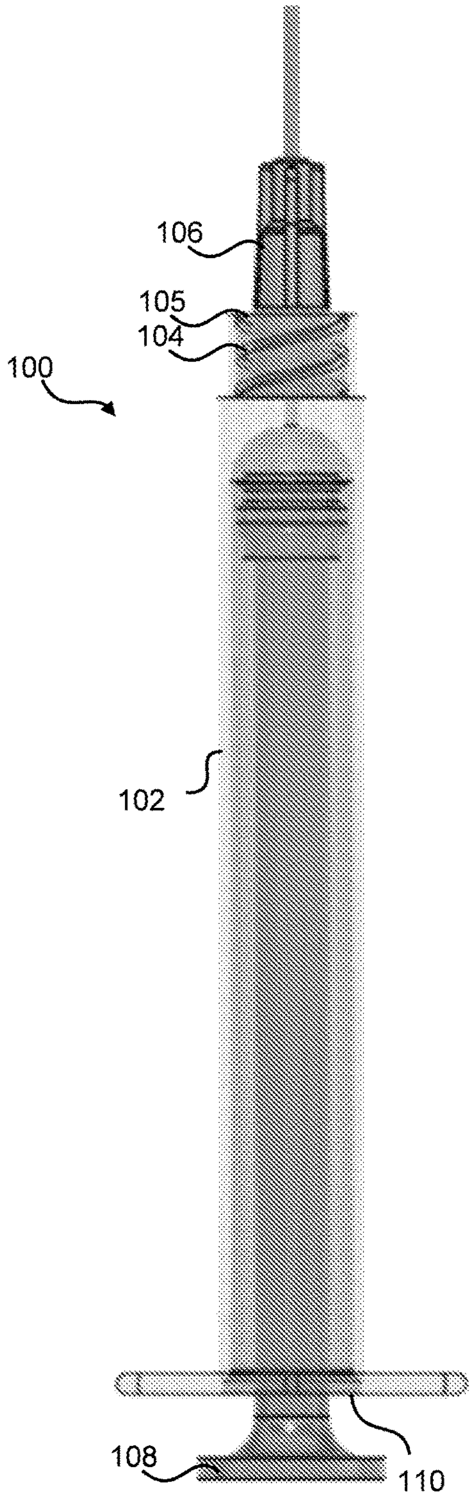
FIG. 1 (PRIOR ART)
FIG. 1 is a schematic perspective view of a syringe, as in the prior art.

The foregoing aspects, features, and advantages of the present disclosure will be further appreciated when considered with reference to the following description of the various embodiments and accompanying drawings. In describing the embodiments of the disclosure as illustrated in the appended drawings, specific terminology will be used for the sake of clarity. The disclosure, however, is not intended to be limited to the specific terms used, and it is to be understood that each specific term includes equivalents that operate in a similar manner to accomplish a similar purpose. Numerous specific details, examples, and embodiments are set forth and described to provide a thorough understanding of various embodiments of the present invention. However, in certain instances, well-known or conventional details are not described in order to provide a concise discussion of embodiments of the present disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Any examples of operating parameters and/or environmental conditions are not exclusive of other parameters/conditions of the disclosed embodiments. Additionally, it should be understood that references to "one embodiment", "an embodiment," "certain embodiments," or "other embodiments" of the present disclosure are not intended to be interpreted as excluding the existence of additional embodiments that also incorporate the recited features. Furthermore, reference to terms such as "above," "below," "upper," "lower," "side," "front," "back," or other terms regarding orientation are made with reference to the illustrated embodiments and are not intended to be limiting or exclude other orientations. As used herein, the term "subject" refers to a person or user receiving an injection. Throughout this description, the term "proximal" refers to the portion of the device or component thereof that is closer to the subject and the term "distal" refers to the portion of the device or component thereof that is farther from the subject. In certain circumstances, the subject may also be a user of the injection device, e.g., syringe. In such circumstances, the terms "proximal" and "distal" are related to the injection site on the subject and not the subject as a whole.

As noted above, FIG. 1 is a schematic perspective view of a syringe 100, as in prior art. The syringe 100 may be considered a standard syringe. The syringe may be comprised of a polymer or plastic, such as polycarbonate or polypropylene. Other materials may be utilized, such as glass or metal, as will be understood by those skilled in the art. The syringe 100, as described above, includes a barrel 102. The barrel 102 is hollow or includes a chamber. The barrel 102 includes a distal end aperture 110 and a proximal end aperture 105. The distal end aperture 110 is of a diameter larger than the proximal end aperture 105. The distal end aperture 110 is adapted to accept a plunger 108 of a corresponding diameter. The plunger 108, when pushed into the barrel 102, ejects the injectable stored in the barrel 102 or chamber of the barrel through the needle nozzle 106. The plunger 108, when withdrawn from the barrel 102, facilitates filling the barrel 102 or chamber with the injectable. In another example, the diameter of the barrel 102, as well as the plunger 108, may vary.

The syringe 100 includes a fitting at the proximal end aperture 105. FIG. 1 illustrates a Luer Lock fitting 104. As such, a needle nozzle (e.g., a hypodermic needle) 106 is attachable to the syringe 100 via the Luer Lock fitting 104. As described above, such a syringe 100 can be used in a typical hypodermic needle injection. Such an injection, if not performed correctly, may cause physical pain and/or damage to a subject. Further, some subjects may exhibit trypanophobia or, in other words, a fear of needles. As such, subjects may refuse needed medical services, solely based on the use of the standard syringe 100 with a needle nozzle 106.

As the needle nozzle 106 is not permanently attached to the syringe 100, other nozzles may be added, for example, needleless nozzles, as will be described herein. Further, such low cost or standard syringes allow for a more widespread accessibility and lower cost of needleless injections.

As noted above, FIG. 2 is a schematic perspective view of a syringe 200 with a needleless nozzle 206 attached, according to an embodiment of the disclosure. The construction or assembly of the syringe 200 may be the same as syringe 100, except, rather than a needle nozzle 106 (e.g., a hypodermic needle), a needleless nozzle 206 is attached to the syringe 200 at the proximal end aperture 105 of the barrel 102 of the syringe 200. Other syringe assemblies may be utilized, such as syringes of varying diameters, varying materials, and/or with varying fittings. The varying fittings may allow for a fluid-impermeable connection of the proximal end aperture 105 and needleless nozzle 206. In an example, the syringe 200 includes a Luer Lock fitting 104. Other varying fittings may include a threaded fitting, custom fittings, a liquid quick disconnect, a hose/barb connection, and/or other fittings. The needleless nozzle 206 may include a corresponding feature to allow for a fluid-impermeable connection between the syringe 200 and the needleless nozzle 206.

Figure 2:
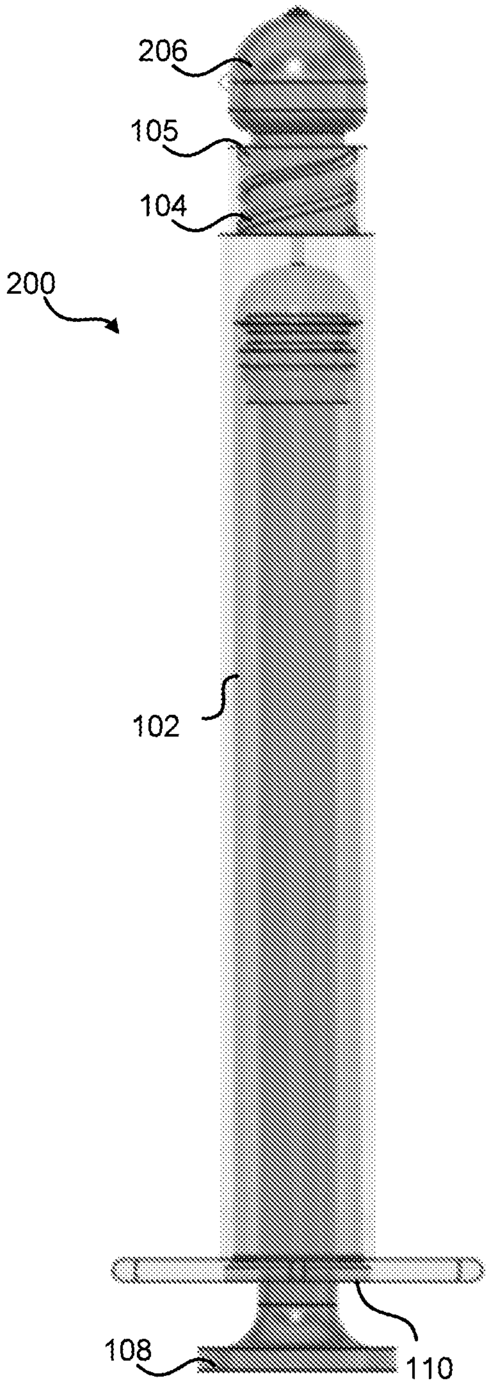
FIG. 2 is a schematic perspective view of a syringe with a needleless nozzle attached, according to an embodiment of the disclosure.

FIG. 2 illustrates a syringe 200 with a needleless nozzle 206 that includes an opening or outlet of about 50 microns to 500 microns. In other embodiments, a needleless nozzle 206 can include an opening or outlet with a range of 150 microns to 200 microns. Such an outlet, in conjunction with the type and/or shape of the plunger 108 and shape of the interior or structure of the barrel 102, when the syringe 200 is utilized, creates the necessary force to enable a needleless injection (e.g., injectable penetrating the subject's skin to a specified level). Stated another way, the shape and/or type of the needleless nozzle 206, the diameter of the outlet of the needleless nozzle 206, the type and/or shape of the plunger 108, and the type and/or shape of the interior of the barrel 102, may affect pressure, force, and/or velocity.

For example, as a linear force is applied to plunger 108, a pressure is created inside the barrel 102 of the syringe 200 and the needleless nozzle 206. Such a pressure may be based on the inner structure of the barrel, the proximal end aperture of the barrel connecting to the needleless nozzle 206, the inner diameter of the needleless nozzle 206, and the diameter of the outlet of the needleless nozzle 206. Based on the linear force, an injectable (e.g., a medication) inside the barrel 102 can be ejected at the outlet of the needleless nozzle 206 at a velocity and force (specified for different medications and/or applications) sufficient to penetrate a subject's skin and deliver the injectable (e.g., medication) to the proper injection level (e.g., to the dermis layer, the subcutaneous layer, or the muscular layer of a subject). The pressures for needleless injection may be in a range of 1 mega Pascal (MPa) to 35 MPa. Based on a specified injection level, varying amounts of linear force may be applied to the plunger 108 (e.g., as deeper injections are specified, larger linear forces may be utilized). The linear forces applied to the plunger 108 may be in a range of 50 newtons (N) to 6000 N. Based on the tensile strength of the syringe 200 and the specified injection level, varying levels of needleless injection may be achieved, without reinforcement of the barrel 102 of the syringe 200. For example, syringe 200 (e.g., a standard syringe) may be capable of withstanding pressure created for an intradermal or subcutaneous injection utilizing the needleless nozzle 206 based on the material used for the syringe 200 (e.g., a material with a sufficient tensile strength), the diameter of the syringe (e.g., the smaller the diameter, the less pressure is created based on the force and/or velocity of the injection), and/or the viscosity of the injectable or medication to be injected (e.g., less force and/or velocity may be utilized for less viscous injectables). The injectable can be a liquid, powder, or other formulation. In some embodiments, the barrel 102 of the syringe 200 may be deigned to withstand pressures required for needleless injection. In certain embodiments, the barrel 102 may be reinforced with an external element such as sleeve 304 (FIG. 3) to prevent the barrel 102 from deforming or bursting during a needleless injection.

In an example, the needleless nozzle 206 can be comprised of plastic, metal, or other suitable material. If comprised of plastic, the needleless nozzle 206 can be manufactured using a process similar to that of manufacturing syringe 200. For example, the needleless nozzle 206 (or any needleless nozzle described herein) can be manufactured by injection molding. The needleless nozzle 206 can be mass manufactured at low cost as compared to customized delivery mechanisms for each of the needleless injection systems.

Figure 3:
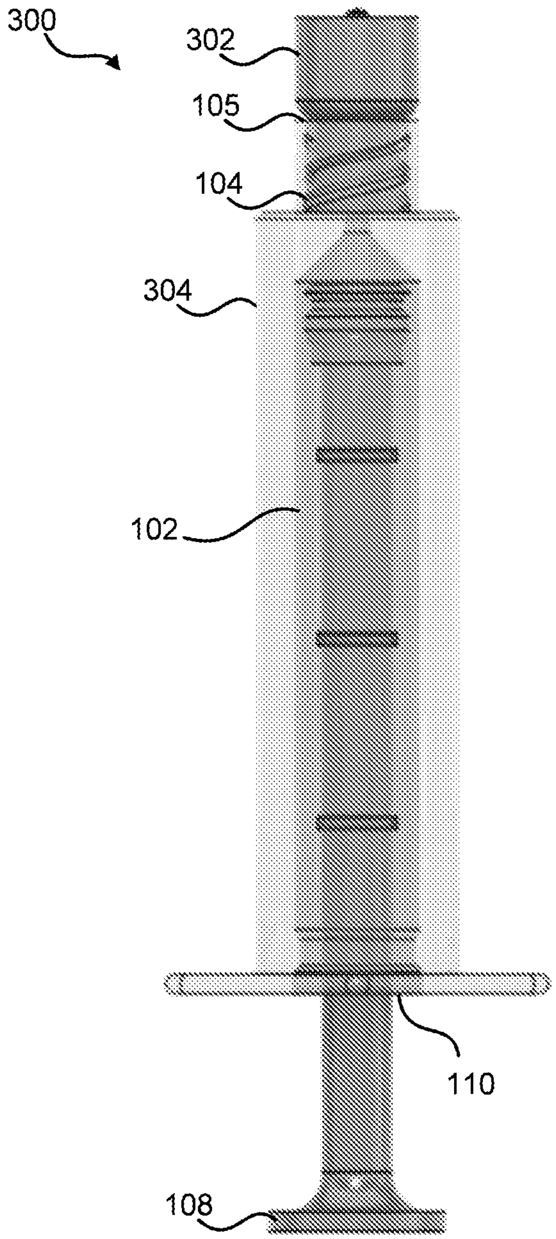
FIG. 3 is another schematic perspective view of a syringe with a needleless nozzle attached and a sleeve fitted over the barrel of the syringe, according to an embodiment of the disclosure.

As noted, FIG. 3 is another schematic perspective view of a syringe 300 with a needleless nozzle 302 attached and a sleeve 304 fitted over the barrel 102 of the syringe 300, according to an embodiment of the disclosure. Syringe 300 can be comprised or assembled similarly to that of syringe 200. In other words, syringe 300 can be a standard syringe. In an example and as noted, such a syringe 300 may deform or burst at high pressure (for example, a large diameter syringe utilizing the force and velocity necessary to perform an intramuscular injection). In such examples, a sleeve 304 or reinforcement can fit over the syringe's 300 barrel 102. Such a sleeve 304 or reinforcement prevents the barrel 102 from deforming or bursting upon injection or ejection, at a high pressure or force, of an injectable stored in the barrel 102. In another example, the sleeve 304 or reinforcement can be comprised of metal, plastic, rubber, or other composite material suitable for preventing deformation. Depending on the type of material used as the sleeve 304 or reinforcement, the thickness of the material may vary. In other words, the sleeve's 304 or reinforcement's thickness may depend upon a tensile strength of varying materials at varying thicknesses, as well as various pressures created by specified needleless injections. For example, a metal sleeve may be substantially stronger than a plastic sleeve, necessitating a thicker plastic sleeve, if utilized. Further, as applications include requirements of withstanding increasing pressures, the thickness of the sleeve may be increased.

In another example and as noted above, a needleless nozzle 302 attaches, via a Luer Lock fitting 104, to the syringe 300. In such examples, the needleless nozzle 302 can include a circumferential spacer to create a space between the subject and the nozzle. In another example, the needleless nozzle 302 can be flat with a slightly raised opening, thus creating a higher force and/or velocity for different medical applications (e.g., intradermal, subcutaneous, or intramuscular needleless injections).

Figure 4:
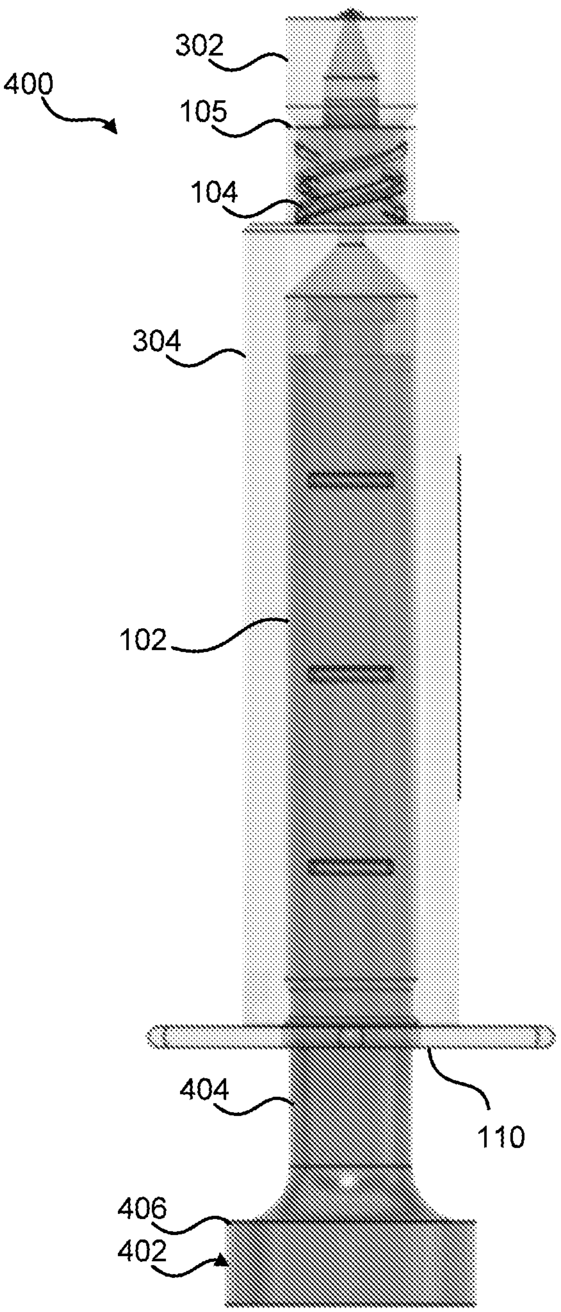
FIG. 4 is another schematic perspective view of a syringe with a needleless nozzle attached, with a sleeve fitted over the barrel of the syringe, and a reinforced plunger according to an embodiment of the disclosure.

FIG. 4 is another schematic perspective view of a syringe 400 with a needleless nozzle 302 attached, with a sleeve 304 fitted over the barrel 102 of the syringe 400, and a reinforced plunger 402, according to an embodiment of the disclosure. Syringe 400 can be comprised of or assembled similar to the previous described syringes. Syringe 400, however, includes a reinforced plunger 402. In an example, the plunger 402 includes a base 406 with greater diameter and thickness than base of plunger 108 and a piston 404 with greater diameter than the embodiment shown in FIG. 3. The piston 404 is configured to linearly translate through a chamber defined by the barrel 102 of the standard syringe 100. In another example, the reinforced plunger 402 can be comprised of plastic, metal, polymer, or of different materials. For example, a plunger 108 may be comprised of plastic. A reinforced plunger 402 may be comprised of other suitable materials, such as metal. In another example, the plunger can be reinforced (e.g., the reinforced plunger 402) to prevent the plunger from breaking or snapping under high linear forces. In other words, while the barrel 102 of the syringe 400 is susceptible to deformation under pressure, the plunger is susceptible to breaking, cracking, snapping, and/or bending under linear forces applied to the plunger. Reinforcing the plunger prevents such damage under high linear force. As noted above, to achieve the pressures within the barrel 102 necessary for needleless injections, the plunger 108 may be subjected to 50 N to 6000 N of linear force. Such forces are likely to break a non-reinforced plunger, e.g., plunger 108. As such, the plunger 108 may be reinforced by modifying the structure, e.g., the thickness or construction, and/or the plunger 108 may be reinforced by using different materials to form the plunger 108.

Figure 5A:
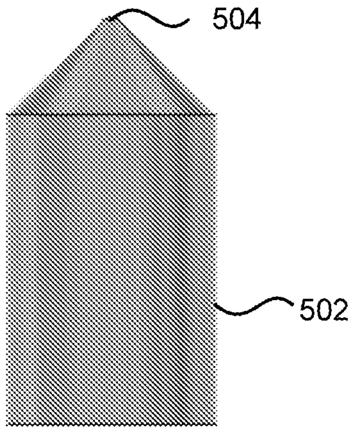
FIGS. 5A, 5B, and 5C are schematic perspective views of a friction fit needleless nozzle, according to an embodiment of the disclosure.
Figure 5B:
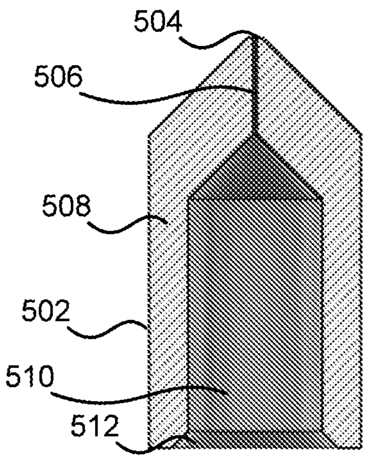
Figure 5C:
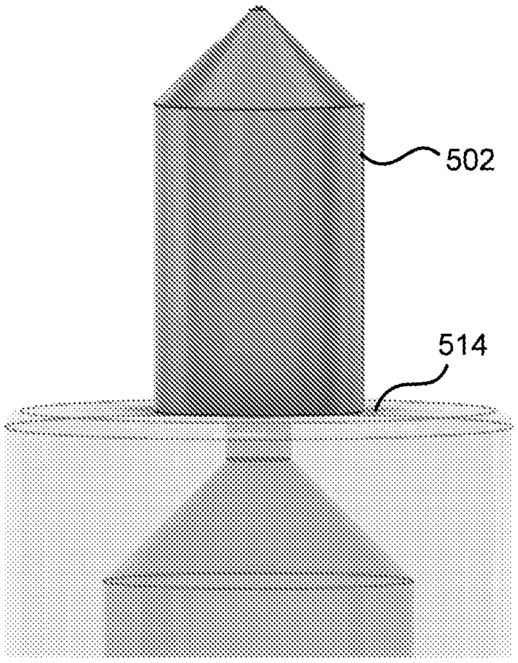

FIG. 5A-5C are schematic perspective views of a friction fit needleless nozzle 502, according to an embodiment of the disclosure. The friction fit needleless nozzle 502 includes a flared aperture 512 corresponding to a friction fit feature of a syringe 514. Other needleless nozzles may include other types of fittings corresponding to fittings on a syringe. Such fittings may include custom fittings, a liquid quick disconnect, a hose/barb connection, or other connections.

In another example, the friction fit needleless nozzle 502 includes an outlet 504 at the tip of the friction fit needleless nozzle 502. The outlet 504 includes a diameter between 100 microns to 1 mm, depending on the application and/or viscosity of the medication to be injected. Further, the friction fit needleless nozzle 502 can, as shown in the cross-sectional view at FIG. 5B, include an inner cavity 510. An injectable flows from the syringe 514 to the inner cavity 510, when a plunger is depressed or inserted into the barrel of the syringe 514. As the injectable may be under a high pressure, due to the force of the plunger, the inner diameter of the syringe 514, and the diameter of pathway 506 to the outlet 504 of the needleless nozzle 502 may include reinforcement walls 508. In another example, as injectable is pushed through the inner cavity 510 of the friction fit needleless nozzle 502, the pressure of the injectable can build to a level such that the injectable is ejected from the needleless nozzle 502 at a force and/or velocity acceptable for a needleless injection.

To create such a force, a plunger may be depressed directly by a user (e.g., a medical provider, such as a doctor or nurse). In other embodiments, to achieve the proper force, pneumatics (e.g., an electro-pneumatic motor or system), hydraulics (e.g., an electro-hydraulic motor or system), an electronic motor or system, or some other suitable mechanism to generate greater force may depress the plunger.

Figure 6A:
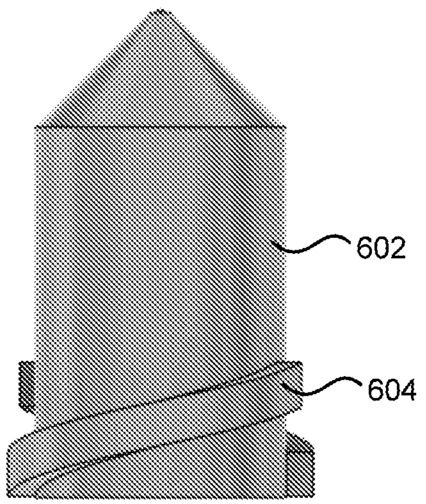
FIGS. 6A and 6B are schematic perspective views of a Luer Lock needleless nozzle, according to embodiments of the disclosure.
Figure 6B:
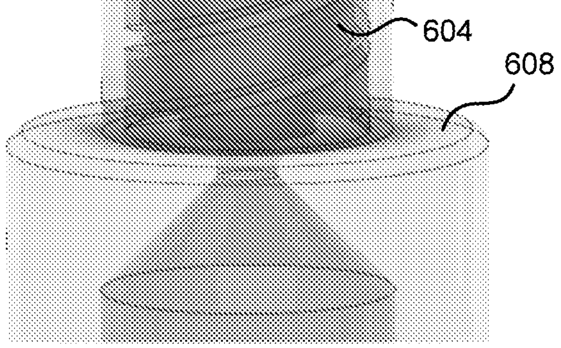

FIG. 6A-6B are schematic perspective views of a Luer Lock needleless nozzle 602, according to an embodiment of the disclosure. As described above, a needleless nozzle can include a Luer Lock fitting (e.g., the Luer Lock fitting 604 of the Luer Lock needleless nozzle 602). In such examples, syringe 608 includes Luer Lock fittings 606 corresponding to the Luer Lock fittings 604 on the Luer Lock needleless nozzle 602. In such examples, the Luer Lock fittings may create an impermeable seal, preventing injectables from leaking between the Luer Lock needleless nozzle 602 and the syringe 608. As noted above, other fittings (e.g., friction fit) may be utilized.

Figure 7A:
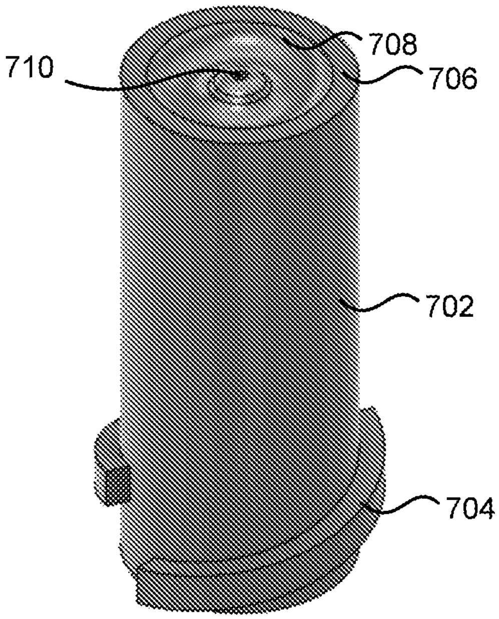
FIGS. 7A and 7B are other schematic perspective views of a Luer Lock needleless nozzle, according to embodiments of the disclosure.
Figure 7B:
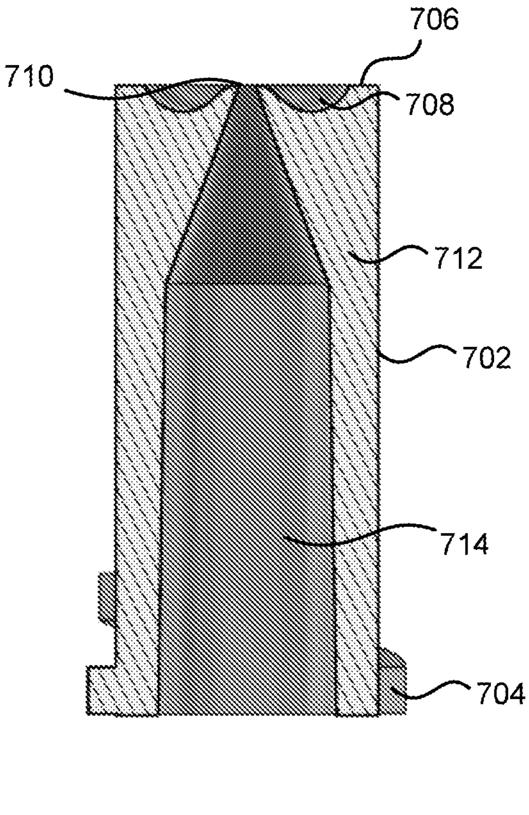
Figures 8A, 8B, 8C, 8D:
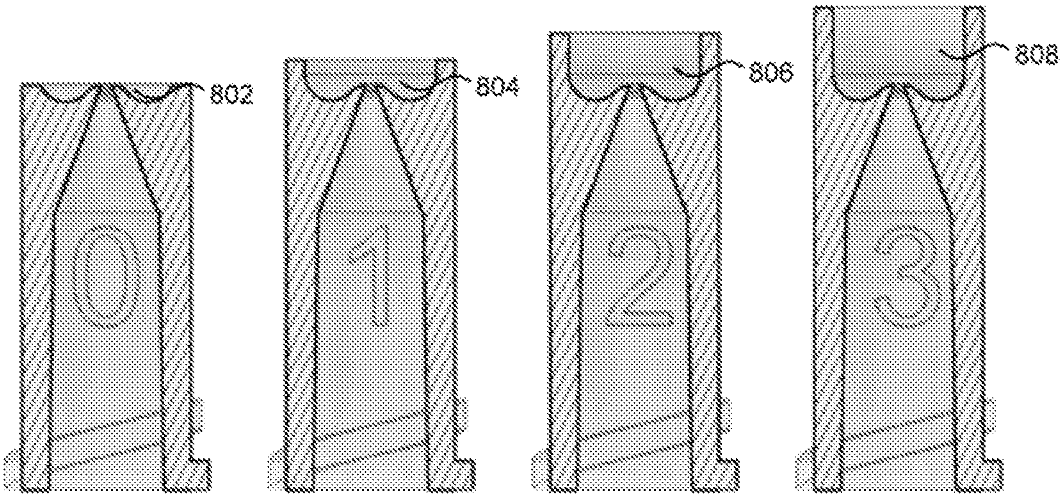
FIGS. 8A, 8B, 8C, and 8D are schematic cross-sectional views of a Luer Lock needleless nozzle, according to embodiments of the disclosure.

FIG. 7A-7B are other schematic perspective views of a Luer Lock needleless nozzle 702, according to an embodiment of the disclosure. Rather than a tapered nozzle, a Luer Lock needleless nozzle 702 can be rounded. Further, rather than a flat top portion, a Luer Lock needleless nozzle 702 can include a spacer 708 between the outer circumference 706 and the outlet 710. The spacer 708 can be between 0 to 3 mm wide. As described above, the Luer Lock needleless nozzle 702 can include Luer Lock fittings 704 corresponding to Luer Lock fittings on a standard syringe. Further, the Luer Lock needleless nozzle 702 can include a cavity 714 and a reinforced wall 712.

FIGS. 8A-8D are schematic cross-sectional views of a Luer Lock needleless nozzle, according to an embodiment of the disclosure. Similar to the Luer Lock needleless nozzle 702, the Luer Lock needleless nozzles of FIGS. 8A-8D include spacers of varying sizes for varying applications. For example, the Luer Lock needleless nozzle labeled as 0 includes a small spacer 802 providing direct contact with a subject. The Luer Lock needleless nozzle labeled 1, 2, and 3 each can include increasing in size spacers 804, 806, and 808. Such spacers may be utilized to alter the force and/or velocity of the injectable ejected from the needleless nozzle. For example, as spacers increase in size, the force and/or velocity of the injectable may decrease, as needed.

Figure 9A:
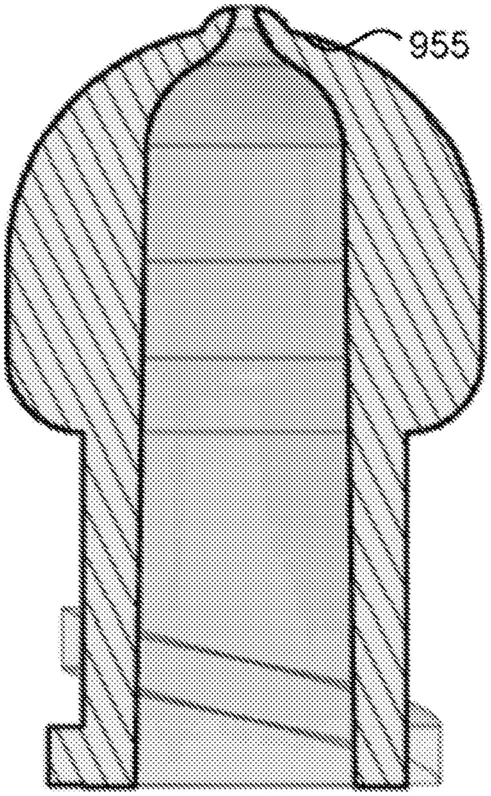
FIGS. 9A and 9B are other schematic cross-sectional views of a Luer Lock needleless nozzle, according to embodiments of the disclosure.
Figure 9B:
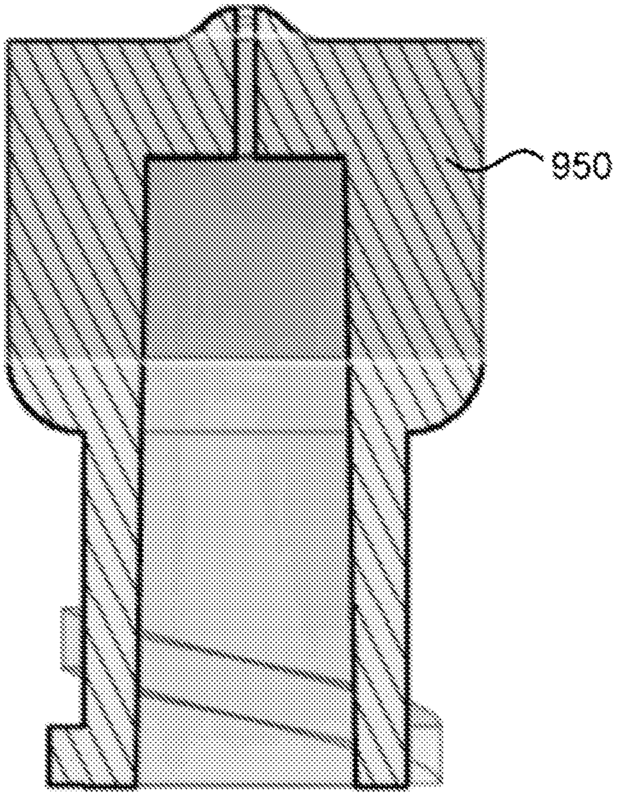

FIGS. 9A and 9B are other schematic cross-sectional views of Luer Lock needleless nozzles 950, 955, according to an embodiment of the disclosure. In such examples, the Luer Lock needleless nozzles 950, 955 may include a similar structure to the previously described Luer Lock needleless nozzles (e.g., including cavities, reinforced walls, outlets, and Luer Lock fittings).

Figure 10A:
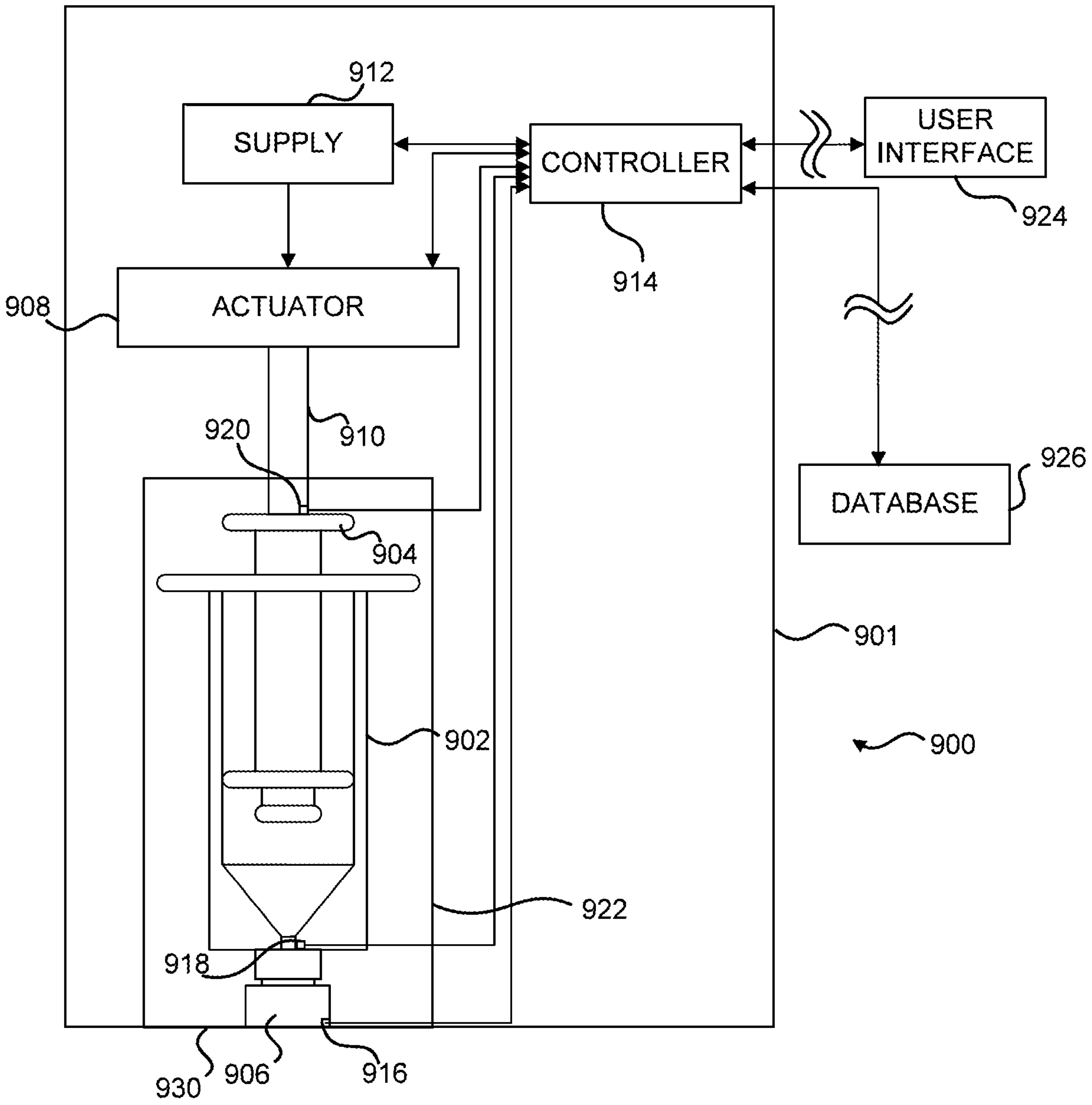
FIGS. 10A and 10B are block diagrams of a needleless injection system, according to embodiments of the disclosure.

FIG. 10A is a block diagram of a needleless injection system 900, according to an embodiment of the disclosure. The needleless injection system 900 includes a housing 901. The housing 901 encloses a standard syringe 902 or retention mechanisms to accept a standard syringe 902. The housing can enclose a piston 910 driven by an actuator 908. The housing 901 can enclose a supply 912 (e.g., a fuel, energy, electric, and/or fluid supply) to allow the actuator 908 to drive (e.g., retract or extend) the piston 910, thus applying a linear force to a plunger 904. The supply 930 can include a fuel or energy supply for the actuator, such as compressed injectable (e.g., gas or liquid) and/or electricity. In some embodiments, the actuator 908 may transfer mechanical energy to the plunger 904 to draw an injectable into the chamber of the barrel and/or to discharge the injectable from the chamber. The supply 930 can connect to the actuator 908 via hoses or other suitable lines as will be understood by those skilled in the art. In other examples, the supply 930 may be external to the housing 901. The housing 901 also encloses controller 914. The controller 914 transmits control signals to the actuator 908 and/or the supply 912 and receives data signals from sensor 916, sensor 918, sensor 920 and/or other sensors disposed within or located around the housing 901. In another example, the housing 901 can enclose the piston 910 or a portion of the piston 910, the actuator 908, the supply 912, and/or the controller 914. In such examples and as will be described in further detail below, the housing 901 can attach to the standard syringe 902. Further, the housing 901 can include a support structure to stabilize the needleless injection system 900.

As noted, the needleless injection system 900 includes an actuator 908. The actuator 908 can include a piston 910. In an example, the actuator 908 and piston 910 can be an electro-pneumatic motor with a piston to apply a linear force to the plunger 904 of the standard syringe 902. In such examples, the controller 914 can transmit a control signal to the electro-pneumatic motor or system (i.e., actuator 908). The control signal may include a signal to retract or extend the piston 910, via compressed air or gas, a distance indicated by the control signal. Further, the control signal may indicate a velocity and/or force for the piston 910 to apply to the plunger 904. In such examples, the electro-pneumatic motor or system (i.e., actuator 908) may utilize compressed air or gas to move the piston 908. In such examples, the supply 912 can include storage of compressed air. In another example, the controller 914 can also transmit control signals, to indicate the amount of compressed air to transfer, to the electro-pneumatic motor or system (i.e., actuator 908). As illustrated, the supply 912 is contained in the housing 901. In another example, the supply 912 can be external to the housing 901. In yet another example, the supply 912 can be contained inside the actuator 908. In such examples, the actuator 908 and supply 912 can be sealed, to prevent leakage of compressed air.

In another example, the actuator 908 and piston 910 can be an electro-hydraulic motor or system. Rather than utilizing compressed air or gas, the electro-hydraulic motor or system (i.e., actuator 912) can utilize a liquid to actuate (e.g., retract or extend) the piston 910. In such examples, the supply 912 can be an injectable source or include an amount of injectable. In such examples, the actuator 908 and supply 912 can be sealed, to prevent leakage of liquids.

The actuator 908 may utilize other mechanisms to transfer force to the plunger 904. For example, the actuator 908 may be an electric motor and the supply 912 a power supply. Other linear actuators may be utilized, as will be understood by those skilled in the art. Further, other motors or actuators to apply a force to the plunger 904 may be utilized, such as reciprocating pumps or motors or other pumps, motors, and/or systems as will be understood by those skilled in the art.

In another example, the housing 901 can include a power supply to provide power to the controller 914. The power supply 912 may be a battery. The battery may include an input connected to the housing 901 to allow for connection to a charger.

As noted, the housing 901 can enclose the piston 910. The piston 910 can include an attachment feature at an end to attach to the plunger 904. In other words, when a standard syringe 902 is added to the housing 901, the end of the piston 910 can connect to the end of the plunger 904. In such examples, the end of the piston 910 can fit over the end of the plunger 904. In another example, the end of the piston 910 can fit into or mechanically attach to the plunger. Such connections may provide stability for the standard syringe 902 and ensure that the plunger 904 does not shift during injection.

As noted, the housing 901 can include a standard syringe 902. As described above, the standard syringe 902 includes a proximal end aperture with a fitting. The fitting can allow for connection of various needleless nozzles, as well as a hypodermic needle. After a standard syringe 902 is used (either once for a subject or multiple times for the same subject), the standard syringe 902 may be removed and another standard syringe added. As noted above, the standard syringe 902 can include a sleeve or reinforcement. In another example, the housing 901 can include an integrated sleeve or reinforcement. In yet another example, the housing 901 can include a removable sleeve or reinforcement. Depending on the size of the standard syringe 902, the removable sleeve or reinforcement can be added or replaced to correspond to the size of the standard syringe 902. In both examples, the standard syringe 902 can be inserted into the sleeve or reinforcement. The standard syringe 902 can be inserted into the housing 901 through an access door 922, panel, or through an opening or aperture in the housing 901. For example, a bottom portion 930 of the housing 901 may include an aperture or opening large enough to allow for syringes of varying size to be inserted into the housing 901 plunger 904 first. In such examples, the bottom portion 930 allows for the needleless nozzle 906 to contact the skin of a subject. In another example, the needleless nozzle 906 can partially or fully protrude through the bottom portion 930 of the housing 901. In another example, the access door 922 may be on the surface adjacent to the bottom portion 930. The access door 922 may lift or slide in a direction to allow for addition and removal of syringes and/or addition and removal of sleeves or reinforcements.

As noted, the housing 901 can enclose a controller 914. The controller 914 may include a processor and memory. The memory may store instructions executable by the processor. As used herein, memory may refer to a machine readable storage medium. As used herein, a "machine readable storage medium" may be any electronic, magnetic, optical, or other physical storage apparatus to contain or store information such as executable instructions, data, and the like. For example, any machine-readable storage medium described herein may be any of random access memory (RAM), volatile memory, non-volatile memory, flash memory, a storage drive (e.g., hard drive), a solid state drive, any type of storage disc, and the like, or a combination thereof. As noted, the machine readable storage medium may store or include instructions executable by the processor.

A processor may include a single processor device and/or a plurality of processor devices (e.g., distributed processors). A processor may be any suitable processor capable of executing/performing instructions. A processor may include a central processing unit (CPU) that carries out program instructions to perform the basic arithmetical, logical, and input/output operations required to execute the method of determining velocity and force for an injection and of determining whether an injection may be initiated or started. A processor may include code (e.g., processor firmware, a protocol stack, a database management system, an operating system, or a combination thereof) that creates an execution environment for program instructions. Processes and logic flows described herein may be performed by one or more programmable processors executing one or more computer programs to perform functions by operating on input data and generating corresponding output.

The controller 914 may include instructions, executable by the controller, to determine the velocity and force of the needleless injection. The determined velocity and force may be based on a force and/or velocity profile. The force and/or velocity profile may be based on a type of medication, amount to be delivered (e.g., a 5 milliliters (mL) of a particular medication), and/or a specified depth of the needleless injection (e.g., intradermal, subcutaneous, or intramuscular). In an example, the velocity and/or force profile may be stored in the controller's 914 memory. In another example, the velocity and/or force profile may be stored in a database 926. In such examples, the controller 914 may connect, via an input/output, to the database 926. The connection may be over an electronic communications network, as the Internet, a Local Area network (LAN), wired network, cable, Wireless Local Area Network (WLAN), cellular, satellite, or other suitable connections that enable the exchange of information between the components of systems, as will be readily understood by one having ordinary skill in the art. In yet another example, the velocity and/or force may be further based on various data points gathered from sensors (e.g., sensors 916, 918, or 920) disposed throughout the housing 901. Velocities utilized for needleless injection can be greater than or equal to 150 meters per second (m/s), for different applications. In another example, the controller 914 may determine the correct placement of the needleless injection system 900, based on various data points gathered from sensors (e.g., sensors 916, 918, or 920) disposed throughout the housing 901. For example, a sensor may sense an amount and/or viscosity of injectable (e.g., medication) included in the standard syringe 902 or the controller 914 may determine the amount and/or viscosity of the injectable (e.g., medication) based on data included in the database 926 or data entered at the user interface 924 (e.g., as a user enters in an ordered medication, the user may include the amount and viscosity of the medication). The controller 914 may determine the force and/or velocity of the needleless injection based on such data (e.g., higher velocity and force may be needed for more viscous injectables). In another example, a sensor may indicate or the controller 914 may include data related to a specific type of needleless nozzle attached to the standard syringe 902 (e.g., the type of needleless nozzle to indicate the depth of injection). The controller 914 may determine the force and/or velocity based on the type of needleless nozzle.

In another example, a user may initiate or start the injection process, via a user interface 924 connected via an input/output to the controller 914. In such examples, the user interface 924 may be a button or touchscreen included on the housing 901. In another example, the user interface 924 may be connected to the input/output via a dedicated or wireless connection. In such examples, the user interface 924 may be a mobile device (e.g. smart phone, tablet, etc.), a desktop computer, a laptop, a wearable computing device, or other type of computing device, as will be readily understood by one having ordinary skill in the art. The user interface 924 may further include a mobile computer application. The user interface 924 may allow for a user to enter in the type or depth of the needleless injection (intradermal, subcutaneous, or intramuscular), an amount of injectable (e.g., medication) to deliver to a subject, and/or other data related to the needleless injection. Further, the housing 901 and/or controller 914 may include a safety mechanism to prevent the initiation or start of the injection. In other words, in response to a signal from the user interface to initiate or start the injection, the housing 901 and/or controller 914 may prevent the initiation or start of the injection until the needleless injection system 900 is correctly positioned. The controller 914 may determine whether an injection may be initiated based on the data received from the sensors (e.g., sensors 916, 918, or 920).

Database 926 may include one or more memory devices that store information and are accessed and managed through or by the controller 914 or processor of the controller 914. For example, databases may include Oracle™ database or other relational databases or non-relational databases such as Hadoop. Databases can include computing components such as database server configured to receive and process requests for data stored in memory devices of databases and to provide data from the databases. The database 926 may be located remotely, such as in a different geographical location or the cloud. The database 926 may include an EMR of the patients, medication data, and/or velocity and/or force profiles.

Figure 10B:
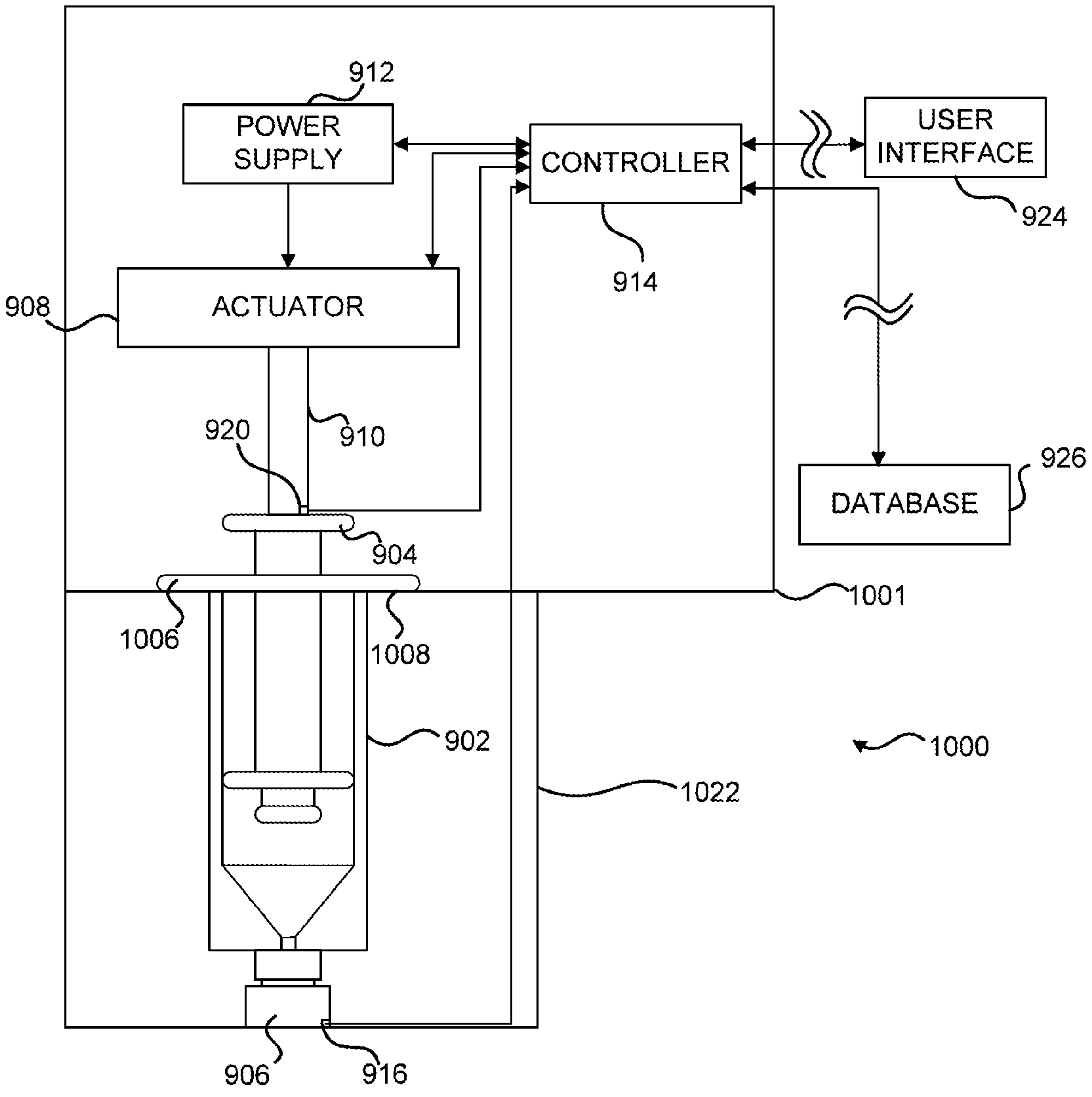

FIG. 10B is a block diagram of a needleless injection system 1000, according to an embodiment of the disclosure. As noted above, the housing 1001 may fit over or attach to a standard syringe 902. The housing 1001 may include an aperture 1008. The aperture 1008 may be smaller than the flange 1006 of the barrel of the standard syringe 902. As the standard syringe 902 is inserted into the aperture 1008 of the housing 1001, the flange 1006 may secure the standard syringe 902 to the housing 1001. In such examples, due to the linear force applied to the standard syringe 902, the flange 1006 may be reinforced. In another example, notches slightly larger than the width of the flange 1006 may secure the flange to the housing 1001, for example, via friction. In another example, mechanical fasteners (e.g., screws, thumbscrews, latches, etc.) may attach the flange 1006 or syringe 902 to the housing 1001. Further, such a housing 1001 may include a stabilizing structure 1022 or rods to prevent the standard syringe from moving during a needleless injection. Further, sensors, such as sensor 916, may be disposed on the stabilizing structure 1022 or rods, to provide data on the location or orientation of the needleless nozzle 906 to the controller 914.

Figure 11:
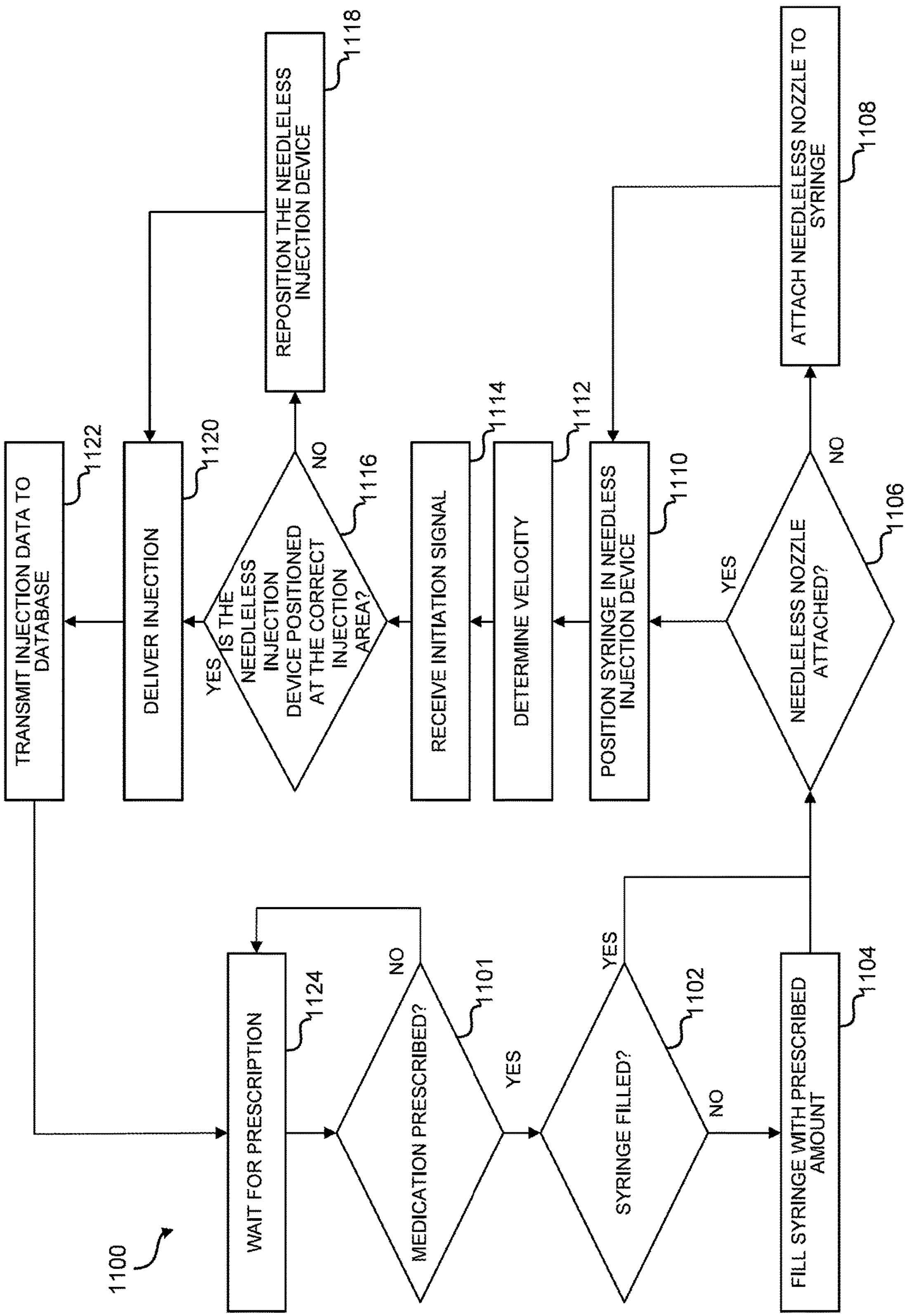
FIG. 11 is a flow diagram for the operation of the needleless injection system, according to an embodiment of the disclosure.

FIG. 11 is a flow diagram for the operation of the needleless injection system, according to an embodiment of the disclosure. The method is detailed with reference to the needleless injection system 900 of FIG. 10A. Unless otherwise specified, the actions of method 1100 may be completed within controller 914. Specifically, method 1100 may be included in one or more programs, protocols, or instructions loaded into the memory of the controller 914 and executed on the processor of the controller 914. The order in which the operations are described is not intended to be construed as a limitation, and any number of the described blocks may be combined in any order and/or in parallel to implement the methods.

At block 1101 the controller 914 can determine whether a medication has been prescribed/ordered. If no medication has been prescribed/ordered, the controller 914, at block 1124 can wait for a prescription/order. When a prescription/order is received, the controller 914 may determine whether a standard syringe 902 is included in the housing 901. The controller 914 may make such a determination based on sensors disposed throughout the housing 901. Sensor 918 and/or sensor 916 may provide data indicating that a standard syringe 902 has been inserted into the housing 901 (or that a housing 901 may be attached to a standard syringe 902).

At block 1102, the controller 914 can determine whether the standard syringe 902 is filled the prescribed/ordered medication. Sensors (e.g., sensor 918 or another sensor disposed at or near the barrel of the standard syringe 902) may provide data indicating whether the standard syringe 902 is filled. In response to a determination that the standard syringe 902 is not filled, the controller 914 may transmit a prompt indicating that the standard syringe 902 requires filling. In another example, a user may position the housing 901, particularly the opening at the needleless nozzle 906 of the standard syringe 902, over the medication (e.g., a bottle or some other storage container including the medication). In such examples, the user may indicate, via the user interface 924, that the medicine is positioned to fill the standard syringe 902. In response to such an indication the controller 914 may send a signal to the actuator 908 and power supply 912 to actuate the piston 910 upwards, thus pulling the plunger 904 up and filling, at block 1104, the standard syringe 902 with the prescribed/ordered amount of medication. In another example, a user may perform block 1104 and fill the standard syringe 902 with the prescribed/ordered amount of medication.

At block 1106, the controller 914 can determine whether the standard syringe 902 includes the needleless nozzle 906. In response to a determination that the needleless nozzle is not attached, the controller 914 may transmit a prompt or indication that a user may connect or attach the needleless nozzle 906 to the standard syringe 902 to continue. In response to a determination that a needleless nozzle 906 is attached to the standard syringe 902 or that a user, at block 1108, has attached the needleless nozzle to the standard syringe 902, at block 1110, if not already included in the housing 901, the controller 914 can transmit a prompt or indication that the standard syringe 902 can be inserted into the housing 901 to continue.

At block 1112, the controller 914 can determine the velocity, as well as the force, that the medication should be delivered at. The controller 914 may determine such a velocity and/or force based on a velocity and/or force profile. In another example, the controller 914 may determine the velocity and/or force based on the type of medication in the standard syringe 902, the amount of medication to be delivered to a subject, the area of the subject that the needleless injection may occur at, the type of needleless nozzle 906, the level or depth that the medication is to be injected to (e.g., intradermal, subcutaneous, or intramuscular injections), and/or other factors.

Once the velocity is determined and the housing 901 is positioned, the controller 914 may wait for an initiation signal. A user may input the initiation signal. At block 1114 the controller 914 can receive an initiation signal. In response to the initiation signal, the controller 914 may determine whether the housing 901 is positioned correctly or at the proper location or area. The controller 914 may also determine whether the housing is positioned properly against the subject (in other words, that the housing is not tilted, but flat against the subject's skin).

In response to a determination that the housing 901 is not properly positioned, the controller 914 may send a prompt or indication for a user to reposition the housing 901 to continue. At block 1118, a user can reposition the housing 901. In response to the repositioning, the controller 914 may re-check or re-evaluate the position of the housing 901. Once the housing 901 is properly positioned the controller 914 may signal to the actuator 908 and power supply 912 the velocity and/or force of the injection. The actuator 908 may proceed to move the piston 910 at the indicated velocity and/or force from the controller 914, thus, at block 1120, delivering the injection.

At block 1122, the controller 914 can transmit data related to the injection to the database 926. Further, a subject's EMR, at the database 926, may be updated with such data. The data related to the injection may include the amount of medication, the date of the injection, the time of the injection, and/or other data related to the injection. Once the data has been transmitted, the controller, at block 1124, can wait for another prescribed/ordered medication.

In the drawings and specification, several embodiments of systems and methods for needleless injection have been disclosed, and although specific terms are employed, the terms are used in a descriptive sense only and not for purposes of limitation. Embodiments of systems and methods have been described in considerable detail with specific reference to the illustrated embodiments. However, it will be apparent that various modifications and changes may be made within the scope of the embodiments of systems and methods as described in the foregoing specification, and such modifications and changes are to be considered equivalents and part of this disclosure.

What is claimed:

1. A needleless injection system, comprising;

a housing including an opening to allow for removal and insertion of a syringe, the syringe comprising a barrel and a plunger, the barrel having a proximal end and an open distal end, the plunger inserted through the open distal end;

a needleless nozzle removeably attached to the proximal end of the barrel;

an actuator connected to the plunger to transfer mechanical energy to the plunger to discharge an injectable from the barrel; and a controller in signal communication with the actuator, the controller configured to determine a velocity and force for an injection based on an amount of a specified injectable for the injection and a level or distance for the injection, the controller configured to transmit the velocity and force to the actuator in response to an initiation of the injection, the needleless nozzle configured to needlelessly inject the injectable contained within the barrel to the level for the injection, the level for the injection being at least the level of an intradermal injection.

2. The needleless injection system according to claim 1, further comprising a sleeve for enclosing the barrel to prevent the barrel from deforming.

3. The needleless injection system according to claim 1, wherein the actuator is capable of transferring mechanical energy to the plunger to draw the injectable into the barrel.

4. The needleless injection system according to claim 1, further comprising a supply in signal communication with the controller, the supply configured to provide energy to the actuator based on a control signal from the controller such that the actuator transfers mechanical energy to the plunger.

5. The needleless injection system according to claim 1, wherein the housing includes a retention mechanism for securing the syringe within the housing.

6. The needleless injection system according to claim 1, further comprising an electro-pneumatic motor having the actuator and a piston.

7. The needleless injection system according to claim 1, further comprising an electrohydraulic motor having the actuator and a piston.

8. The needleless injection system according to claim 1, wherein the actuator includes an electric motor.

9. The needleless injection system according to claim 1, wherein the controller is in signal communication with a database, the database including a velocity profile.

10. The needleless injection system according to claim 9, wherein the controller further determines velocity based on the velocity profile.

11. A needleless injection system, comprising;

a housing including an opening to allow for removal of and insertion of a standard syringe, the standard syringe comprising a barrel and a plunger, the barrel having a proximal end and an open distal end, the plunger insertable through the open distal end;

a needleless nozzle removeably attached to the proximal end of the barrel, the needleless nozzle configured for needleless injection of an injectable contained within the barrel;

an actuator including a piston disposed within the housing, the piston configured to physically interact with the plunger to translate the plunger relative to the barrel; and a controller in signal communication with the actuator, the controller configured to determine a velocity and force for an injection based on an amount of the injectable for the injection and a level for the injection, the controller configured to transmit the velocity and force to the actuator in response to an initiation of the injection, the actuator configured to translate the plunger based on the velocity and the force transmitted thereto to inject the injectable into a subject at the level for the injection, the level for the injection being at least the level of an intradermal injection.

12. The needleless injection system according to claim 11, further comprising an integrated sleeve for enclosing the barrel to prevent the barrel from deforming.

13. The needleless injection system according to claim 11, further comprising a supply in signal communication with the controller, the supply configured to provide energy to the actuator based on a control signal from the controller such that the piston of the actuator translates the plunger.

14. The needleless injection system according to claim 11, wherein the housing includes a retention mechanism to secure the standard syringe within the housing.

15. A needleless injection system for a standard syringe including a barrel having a proximal end, the needleless injection system comprising;

a needleless nozzle configured to removeably attach to the proximal end of the barrel, the needleless nozzle configured to generate force necessary to enable needleless injection into a subject to at least a level of an intradermal injection from a standard syringe.

16. The needleless injection system according to claim 15, wherein the needleless nozzle is configured to frictionally attach to the proximal end of the barrel.

17. The needleless injection system according to claim 15, wherein the needleless nozzle includes a fitting configured to interface with a complementary fitting of the proximal end of the barrel.

18. The needleless injection system according to claim 15, wherein the needleless nozzle defines an outlet having a diameter in a range of 50 microns to 500 microns.

19. The needleless injection system according to claim 15, further comprising a sleeve configured to receive the barrel therein, the sleeve for preventing deformation of the barrel.

20. The needleless injection system according to claim 15, further comprising a reinforced plunger capable of producing linear forces within the barrel suitable for intradermal, subcutaneous, or intramuscular needleless injection.

* * * * *